(12) United States Patent
López Nieto et al.

(10) Patent No.: US 7,355,062 B2
(45) Date of Patent: Apr. 8, 2008

(54) CATALYST FOR SELECTIVE OXIDATION AND AMOXIDATION OF ALKANES AND/OR ALKENES, PARTICULARLY IN PROCESSES FOR OBTAINING ACRYLIC ACID, ACRYLONITRILE AND THE DERIVATIVES THEREOF

(75) Inventors: Jose Manuel López Nieto, Valencia (ES); Pablo Botella Asunción, Valencia (ES); Benjamín Solsona Espriu, Valencia (ES)

(73) Assignees: Consejo Superior de Investigaciones Cientificas, Madrid (ES); Universidad Politecnica de Valencia, Valencia (ES)

( * ) Notice: Subject to any disclaimer, the term of this patent is extended or adjusted under 35 U.S.C. 154(b) by 461 days.

(21) Appl. No.: 10/759,384

(22) Filed: Jan. 16, 2004

(65) Prior Publication Data

US 2004/0230070 A1    Nov. 18, 2004

Related U.S. Application Data

(63) Continuation of application No. PCT/ES02/00357, filed on Jul. 16, 2002.

(30) Foreign Application Priority Data

Jul. 17, 2001    (ES)    ................................ 200101756

(51) Int. Cl.
*C07C 255/08*    (2006.01)
*C07C 51/16*    (2006.01)

(52) U.S. Cl. ...................................... 558/466; 562/549

(58) Field of Classification Search ................ 562/549; 502/312; 558/466
See application file for complete search history.

(56) References Cited

U.S. PATENT DOCUMENTS

| | | |
|---|---|---|
| 5,198,580 A | 3/1993 | Bartek et al. |
| 5,380,933 A | 1/1995 | Ushikubo et al. |
| 5,994,580 A | 11/1999 | Takahashi et al. |

FOREIGN PATENT DOCUMENTS

| | | |
|---|---|---|
| EP | 0 031 693 | 7/1981 |
| EP | 0 489506 A1 | 6/1992 |
| EP | 0529853 | 8/1992 |
| EP | 0608838 | 1/1994 |
| EP | 0895809 | 8/1998 |
| EP | 0962253 | 5/1999 |
| EP | 0 962 253 A2 | 12/1999 |
| EP | 0 970942 A1 | 1/2000 |
| EP | 0 997454 A1 | 5/2000 |
| ES | 2 061 572 | 12/1994 |
| FR | 2 754 817 | 10/1997 |
| WO | PCT/JP97/04169 | 11/1997 |
| WO | PCT/JP98/03151 | 7/1998 |

OTHER PUBLICATIONS

Hiromu Watanabe et al, New Synthesis route for Mo-V-Te mixed oxides catalyst for propane ammoxidation, Applied Catalysis A: General 194-195 (2000) 479-485.
Manhua Mandy Lin, Selective oxidation of propane to acrylic acid with molecular oxygen, Applied Catalysis A: General 207 (2001) 1-16.

*Primary Examiner*—James O. Wilson
*Assistant Examiner*—Ebenezer Sackey
(74) *Attorney, Agent, or Firm*—Klauber & Jackson L.L.C.

(57) ABSTRACT

A catalyst for the selective oxidation and amoxidation of alkanes and/or alkenes, particularly in processes for obtaining acrylic acid, acrylonitrile and derivatives of these, including a least one oxide of Mo, Te, V, Cu and at least another A component selected from among Nb, Ta, Sn, Se, W, Ti, Fe, Co, Ni, Cr, Ga, Sb, Bi, a rare, alkaline or alkali-earth earth, in such a way that the catalyst presents, in a calcined form, an X-ray diffractogram with five intensive diffraction lines, typically the most intense corresponding to diffraction angles of 2θ at 22.1±0.4, 27.1±0.4; 28.1±0.4, 36.0±0.4 and 45.1±0.4.

Figure 1:
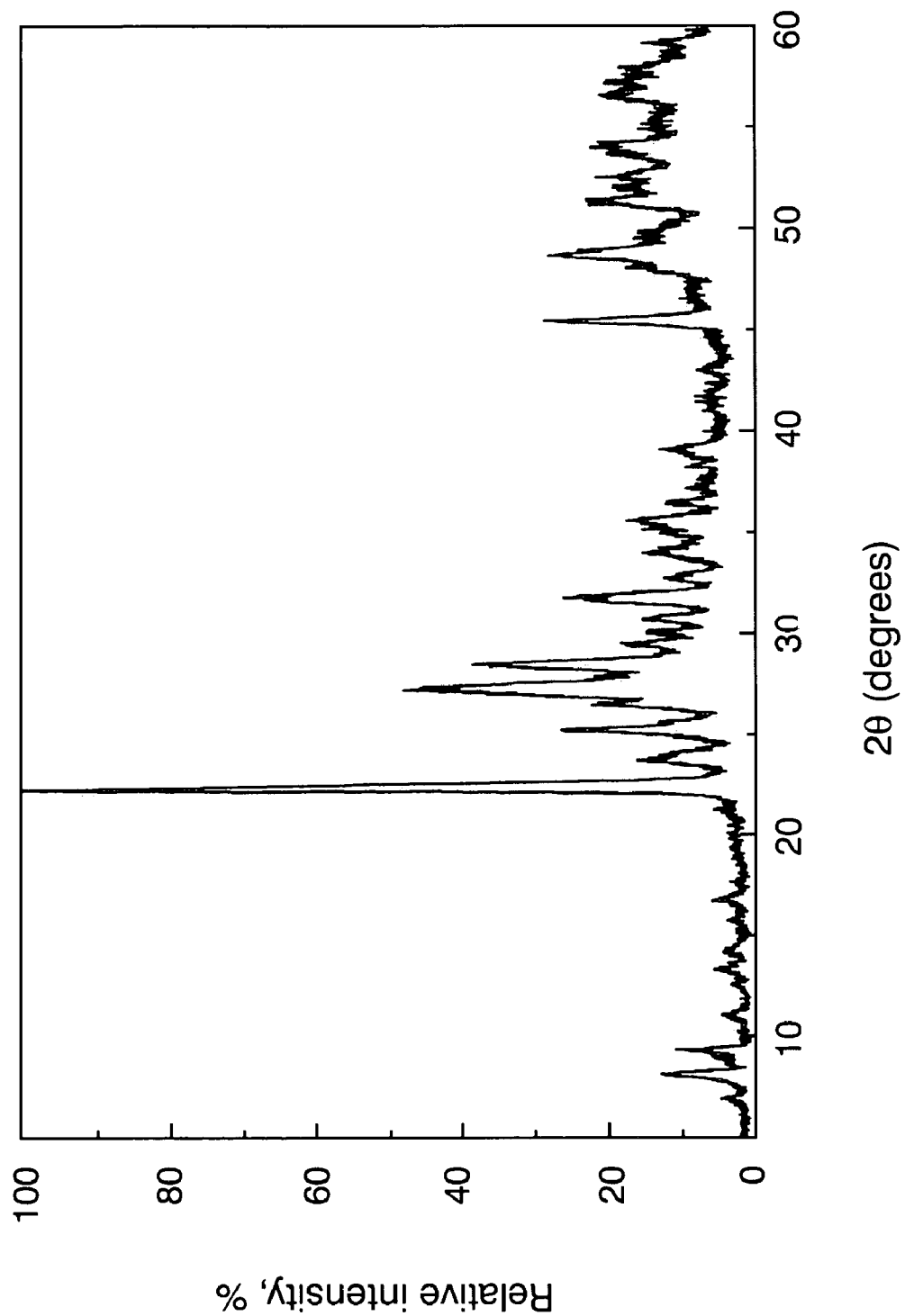

In the preferred embodiment, the catalyst has the following empiric formula:

$$MoTe_hV_iCu_jA_kO_x$$

in which h, i, j, k are values comprised between 0.001 and 4.0 and x depends on the oxidation status or valency of the Mo, Te, V, Cu and A elements.

9 Claims, 8 Drawing Sheets

CATALYST FOR SELECTIVE OXIDATION AND AMOXIDATION OF ALKANES AND/OR ALKENES, PARTICULARLY IN PROCESSES FOR OBTAINING ACRYLIC ACID, ACRYLONITRILE AND THE DERIVATIVES THEREOF

RELATED APPLICATIONS

The present application is a Continuation of co-pending PCT Application No. PCT/ES02/00357, filed Jul. 16, 2002, which in turn, claims priority from Spanish Application Serial No. 200101756, filed Jul. 17, 2001. Applicants claim the benefits of 35 U.S.C. §120 as to the PCT application and priority under 35 U.S.C. §119 as to said Spanish application, and the entire disclosures of both applications are incorporated herein by reference in their entireties.

TECHNICAL FIELD OF THE INVENTION

This invention is comprised in the technical field of catalysts in petrochemistry and in selective oxidation and amoxidation of alkanes and alkenes. It also belongs to the sector of catalysts for processes for obtaining acrylic acid, acrylonitrile and derivatives of these.

STATE OF THE ART PRIOR TO THE INVENTION

Unsaturated α,β carboxylic acids, such as acrylic acid or methacrylic acid are monomers of industrial interest for obtaining synthetic resins and plastics. In general, these acids are obtained through direct oxidation of an olefin (propylene or isobutylene) with oxygen (or air) and high temperatures in the presence of a catalyst. They can also be obtained from unsaturated α,β aldehydes (acrolein or methacrolein) through oxidation in the gaseous phase in the presence of a catalyst.

For economic reasons, it is of industrial interest to substitute olefins by saturated hydrocarbons.

Catalysts based on metal oxides with molybdenum and/or vanadium for the oxidation of propane are described in the U.S. Pat. No. 5,198,580, although the yield of acrylic acid achieved with this type of catalyst is low.

The Mo-V-Te-Nb metal oxides are more effective for selective oxidation of propane to acrylic acid as gathered, for example, from T. Ushikubo et al., U.S. Pat. No. 5380933; EP-608838-B1, M. Lin, M. W. Linsen, EP-A-0962253; S. Komada, H. Hinago, M. Kaneta, M. Watanabe, EP-A-0895809.

The metal oxide system based on Mo—V—Te—Nb—X has also been proposed as an effective system where X can be another chemical element. Thus, in the U.S. Pat. No. 5,380,933 and in the related patent applications EP-0608838, WO-A-98/22421 and WO-A-99/3825, a catalytic system is proposed characterised by their Mo—V—Te—X—O composition, where X is Nb, Ta, W, Ti Al, Zr, Cr, Mn, Fe, Ru, Co, Rh, Ni, Pd, Pt, Sb, Bi, B, In, Ce, and by its crystalline structure defined by an X-ray diffractogram with diffraction angles of 2θ at 22.1, 28.2, 36.2, 45.2, 50.0. The AMNXO system is proposed in the European patent application EP-A-0962253 where A=Mo, W, Fe, Nb, Ta, Zr; M=V, Ce, Cr; N=Te, Bi, Sb, Se; X=Nb, Ta, W, Ti, Al, Zr, Cr, Mn, Fe, Ru, Co, Rh, Ni, Pd, Pt, Sb, Bi, B, In, Ce.

These catalysts are similar to others proposed for obtaining acrylonitrile through the amoxidation of propane such as those proposed by T. Ushikubo, K. Oshima, A. Kayo, T. Umezawa, K. Kiyono, I. Sawaki (EP-A-0529853). Likewise, both the type of element proposed and the crystalline structure of the catalytic system are similar to those indicated beforehand for obtaining acrylic acid.

However, the method of preparation and the composition of the conventional catalysts appear to have a great influence on the catalytic properties of these materials (M. M. Lin, Appl. Catal. A 207, 1, 2001; H. Watanabe, Y. Koyasu, Appl. Catal. A 1994-195, 479, 2000). In this sense, the patent EP-A-0962253 refers to a method in the preparation of MoVTeNb catalysts that is different from that proposed in the U.S. Pat. No. 5,380,933 patent and in the related applications for patents EP-0608838, WO-A-98/22421 and WO-A-99/3825.

Also, the Mo—V—Sb—A metal oxides (where A can be Nb, Ta, Sn, W, Ti, Ni, Fe, Cr or Co) appear to be effective in the oxidation of propane to acrylic acid (M Takayashi, X. Tu, T. Hirose, M. Ishii, FR-A-2754817; U.S. Pat. No. 5,994,580). In the case of these catalysts, a selectivity of 72.6% acrylic acid was obtained for a 35% conversion of propane.

DESCRIPTION OF THE INVENTION

The present invention refers to a catalyst for the selective oxidation and amoxidation of alkanes and/or alkenes, particularly in processes for obtaining acrylic acid, acrylonitrile and derivatives of these, whose catalyst, besides Mo, Te, V and at least another A component selected from among Nb, Ta, Se, W, Ti, Fe, Co, Ni, Cr, Ga, Sb, Bi, a rare, alkaline or alkali-earth earth, also comprises Cu, in such a way that at least Mo, Te, V and Cu are present at least in the form of at least an oxide, preferably a mixed calcined oxide, the catalyst presenting in a calcined form, an X-ray diffractogram with five intensive diffraction lines, typically the most intense corresponding to diffraction angles of 2θ at 22.1±0.4, 27.1±0.4; 28.1±0.4, 36.0±0.4 and 45.1±0.4.

In the preferred embodiment, the catalyst has the following empiric formula:

$MoTe_hV_iCu_jA_kO_x$ in which h, i, j, k are values comprised between 0.001 and 4.0 and x depends on the oxidation status or valency of the Mo, Te, V, Cu and A elements, that is to say, the amount x of oxygen of the catalyst can depend on the composition and activation method. In this embodiment, preferably:

h and i are comprised between 0.01 and 3, preferably between 0.02 and 2 the i/h ratio is comprised between 0.3 and 10 j is comprised between 0.001 and 2, preferably between 0.001 and 0.5, and k is comprised between 0.001 and 2.

On the other hand, when A is Nb or Ta in this emobodiment, preferably h and i are comprised between 0.02 and 2, the i/h ratio is comprised between 0.3 and 10, j is comprised between 0.001 and 1.5 and k is comprised between 0.001 and 2

According to the invention, the catalyst can be a mixed oxide supported on a solid such as, for example, silica, aluminium oxide, titanium oxide and mixtures of these, silica can be present in a proportion of 20 to 70% by weight of the total weight of the catalyst. On the other hand, in its calcined form, the catalyst according to the invention can be in the form of a mixed oxide supported on silicon carbide.

Typically, in its calcined form, the catalyst according to the invention has an X-ray diffractogram whose five most intensive diffraction lines, together with the corresponding intensities relating to the peak of greatest intensity, are those shown in Table 1.

TABLE 1

| 2θ angle of diffraction (±0.4) | Average spacing (A) | Relative intensity |
|---|---|---|
| 22.1 | 4.02 | 100 |
| 27.1 | 3.29 | 20-120 |
| 28.1 | 3.17 | 20-120 |
| 36.0 | 2.49 | 10-50 |
| 45.1 | 2.01 | 20-60 |

The catalyst in the present invention can be used particularly in
- selective oxidation processes for propane to acrolein and/or acrylic acid, in the gaseous phase and in the presence of water vapour,
- processes for obtaining acrylic acid through a reaction of propylene and oxygen in the gaseous phase and in the presence of water,
- processes for obtaining acrylonitrile through a propylene and/or propylene and oxygen reaction, in the gaseous phase in the presence of ammonia and water vapour, and
- processes for obtaining methacrylic acid through an isobutene and/or isobutylene reaction with oxygen in the gaseous phase and in the presence of water.

The method for the inclusion of copper in the catalyst and the optimum content of copper depends on the method for preparing the catalyst and/or the composition of the other elements.

The catalyst in the present invention can be prepared by conventional methods from aqueous solutions of the different elements with the desired atomic relations, and also by employing hydrothermal methods (containing two or more elements in the synthesis, particularly containing Mo and Te). The synthesis temperature and time can be determining. Thus, the synthesis temperature is preferably between 100 and 250° C. and, more precisely, between 150 and 180° C. The synthesis time is, preferably, between 6 and 500 hours, and more precisely between 24 and 200 hours.

The main elements, such as salts, oxides, hydroxides, chlorides or alkoxides can be incorporated pure or as mixtures or two or more elements:
Mo: molybdic acid, ammonium molybdate, ammonium hepta-molybdate, molybdenum oxide;
Te: telluric acid, telurium oxide, metallic telurium;
V: ammonium vanadate, vanadium oxide, vanadyl sulphate, vanadyl oxalate, vanadyl chloride;
Cu: copper nitrate, copper oxide, copper oxalate, copper sulphate.

The elements Nb, Ta, Sn, Se, W, Ti, Fe, Co, Ni, Cr, Ga, Sb, Bi, rare earth, alkaline or alkali-earth, can also be incorporated as pure salts, oxides, hydroxides, chlorates or alkoxides, oxalates or mixtures of two or more elements, although they preferably have been incorporated as salts.

Once the different elements have been mixed (either in a solution or by hydro-thermal treatment), the solid is dried and calcined. Drying is performed by conventional methods in a stove, evaporation with stirring, evaporation in a Rotavapor or vacuum drying. The dry solid is calcined in the presence of an inert gas such as, for example, nitrogen, helium, argon or mixtures. Calcination can be carried out by passing a flow of inert gas (with spatial speeds of between 1 and 400 h$^{-}$1) or static. The temperature is preferably between 350 and 800° C. The calcination time is not determining but is preferred between 0.5 hours and 20 hours. The speed of heating is not determining but is preferred between 0.1° C./minute and 10° C./minute.

Although the catalyst can be used as described in this description, or could also be used supporting it on a solid such as: silica, aluminium oxide, titanium oxide and mixtures of these and also on silicon carbide. In these cases, the fixing of the different catalyst elements on the support can be performed by conventional impregnation methods (pore volume, solution excess) or simply by precipitation of a solution containing the active elements on the support.

This catalyst is particularly active for the selective oxidation and amoxidation of alkanes and/or alkenes. Propane and/or isobutane can be employed as alkanes. Propylene and/or isobutylene as olefins. Pure oxygen, oxygen-inert gas mixtures (with a different proportion of the two) or air enriched with oxygen can be employed as an oxidising agent. The water may be incorporated in the supply in the oxidising process, or not, although, generally, an increase is observed of the selectivity towards acrylic acid when the reaction is carried out in the presence of water vapour. The water content in the reaction mixture can be from 0 at 80% and more preferably between 20 and 60%.

The presence of ammonia and water is required in the amodixation process as well as the gases described for oxidation. The concentration of ammonia in the reaction mixture can be from 2 to 40%, but preferably between 8 and 15%.

Both the oxidation and the amoxidation process can be carried out in a fixed bed reactor or a fluidised bed reactor. The reaction temperature is between 250 and 550° C., preferably between 300 and 480° C., and more preferably between 350 and 440° C. The contact time defined as the ratio between the catalyst volume and the total flow of gases supplied is between 0.001 and 100 s. Although the contact time depends on the method of preparation and the composition of the catalyst employed, in general it is preferable between 0.05 and 50, and more preferably between 0.1 and 25 s.

MEANS OF CARRYING OUT THE INVENTION

Aspects of the invention based on some examples will be described below:

EXAMPLE 1

Preparation of an Oxidising Catalyst From a Solution That Contains Mo—V—Te—Nb to Which a Copper Salt Has Been Added 120.0 g of tetra-hydrated ammonium hepta-molybdate, 23.80 g of ammonium metavanadate and 35.96 g of telluric acid were dissolved in 1960 ml of hot water at 80° C. obtaining a uniform solution. On the other hand, and after heating to 40° C., a solution (535.2 g) of niobium oxalate was prepared which contained 80.96 millimoles of niobium and added to the previous solution obtaining a solution. The water was removed from this solution with a Rotavapor at 50° C., obtaining a solid. This solid was dried in a stove at 110° C. for 24 hours and ground until it reached particle sizes of less than 0.25 mm. The resulting powder was calcined at 600° C. for 2 hours in a nitrogen environment.

10.0 g of the calcined solid are added to 10 ml of an aqueous solution with 0.305 g of copper nitrate (II). The solid resulting after the evaporation of the excess water, with stirring at 80° C., was dried in a stove at 110° C. for 24 hours and ground until it reached particle sizes of less than 0.25 mm. The resulting powder was calcined at 600° C. for 1 hour in a nitrogen environment to obtain the catalyst. The catalyst presents an X-ray diffractogram as shown in FIG. 1.

EXAMPLE 2

Use of the Catalyst Described in Example 1 for Selective Oxidation of Propane to Acrylic Acid 6.0 g of the catalyst described in example 1 were put in a fixed bed quartz reactor. The oxidation reaction was carried out employing a mixture of gases, with a molar relation of propane: oxygen: helium: water=4:8:58:30, at a reaction temperature of 380° C. and a contact time of 4 s. The results obtained are shown in table 2.

EXAMPLE 3

Figure 2:
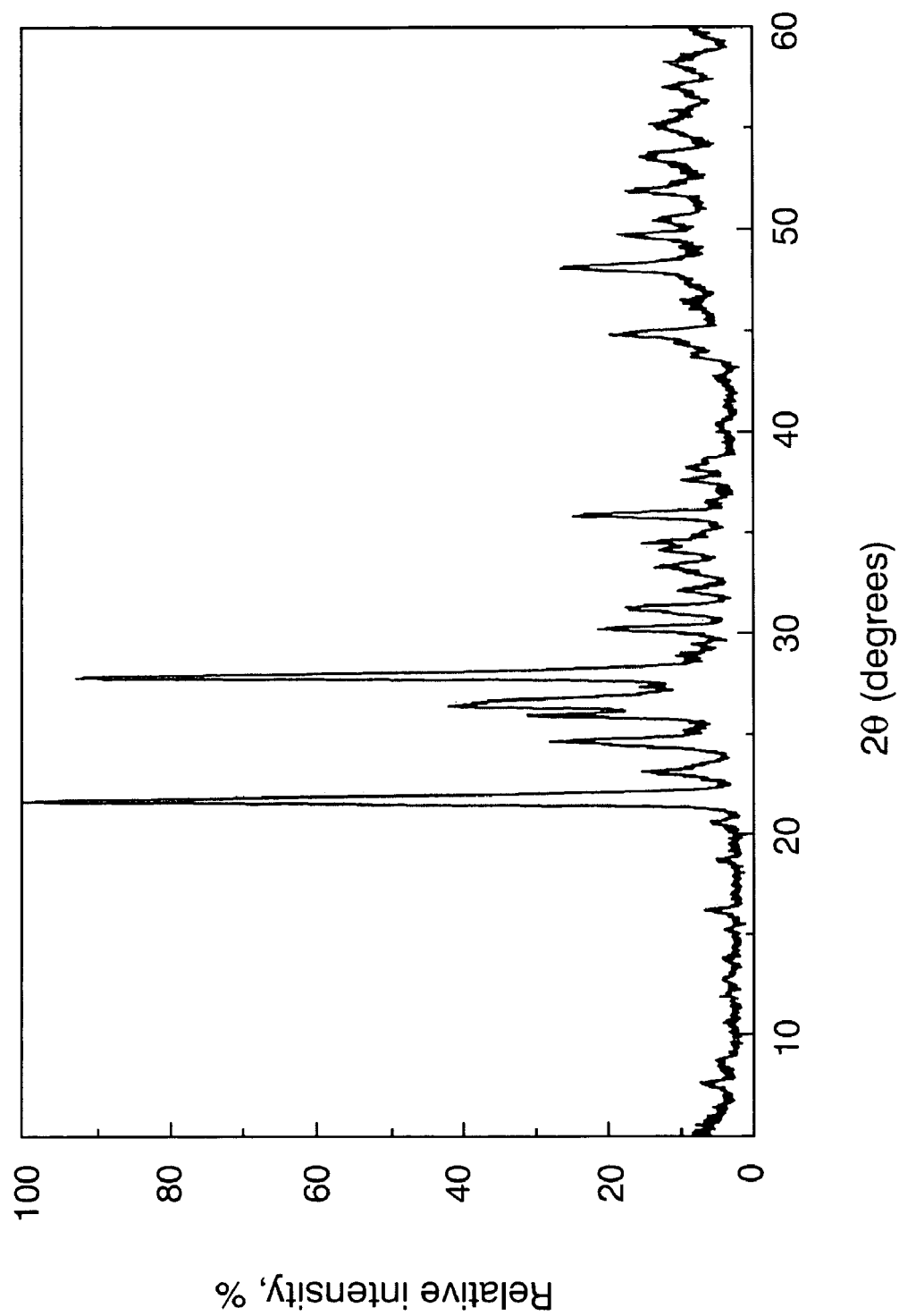

Preparation of an Oxidation Catalyst From a Solution That Contains Mo—V—Te—Nb Without the Incorporation of a Copper Salt 120.0 g of tetra-hydrated ammonium hepta-molybdate, 23.80 g of ammonium methavanadate and 35.96 g of telluric acid were dissolved in 1960 ml of hot water at 80° C. obtaining a uniform solution. On the other hand, and after heating to 40° C., a solution (535.2 g) of niobium oxalate was prepared which contained 80.96 millimoles of niobium and added to the previous solution obtaining a solution. The water was removed from this solution by evaporation with a Rotavapor at 50° C., obtaining a solid. This solid was dried in a stove at 110° C. for 24 hours and ground until it reached particle sizes of less than 0.25 mm. The resulting powder was calcined at 600° C. for 2 hours in a nitrogen environment to obtain the catalyst. FIG. 2 shows the X-ray diffractogram for this catalyst.

EXAMPLE 4

The Use of the Catalyst Described in Comparative Example 3 for the Selective Oxidation of Propane to Acrylic Acid is Shown in This Example 12.0 g of the catalyst described in comparative example 1 were put in a fixed bed quartz reactor. The oxidation reaction was carried out employing a mixture of gases, with a molar relation of propane: oxygen: helium: water=4:8:58:30, at a reaction temperature of 380° C. and a contact time of 9.6 s. The results are shown in table 2. From the results obtained it was shown that the addition of the copper in the composition of the catalyst produces an increase both in the conversion of propane and in the selectivity towards acrylic acid.

EXAMPLE 5

Preparation of an Oxidation Catalyst Similar to That in Example 1 to Which a Lower Amount of Copper Was Added 120.0 g of tetra-hydrated ammonium hepta-molybdate, 23.80 g of ammonium methavanadate and 35.96 g of telluric acid were dissolved in 1960 ml of hot water at 80° C. obtaining a uniform solution. On the other hand, and after heating to 40° C., a solution (535.2 g) of niobium oxalate was prepared which contained 80.96 millimoles of niobium and added to the previous solution obtaining a solution. The water was removed from this solution by evaporation with a Rotavapor at 50° C. obtaining a solid. This solid was dried in a stove at 110° C. for 24 hours and ground until it reached particle sizes of less than 0.25 mm. The resulting powder was calcined at 600° C. for 2 hours in a nitrogen environment.

10.0 g of calcined solid were suspended in 10 ml of an aqueous solution with 0.152 g of copper nitrate (II). The water was evaporated with stirring at 800° C. The solid resulting was dried in a stove at 110C for 24 hours and ground until it reached particle sizes of less than 0.25 mm. The resulting powder was calcined at 600° C. for 1 hour in a nitrogen environment to obtain the catalyst.

EXAMPLE 6

The Use of the Catalyst Described in Example 5 for the Selective Oxidation of Propane to Acrylic Acid 6.0 g of the calcined solid described in example 1 were put in a fixed bed quartz reactor. The oxidation reaction was carried out employing a mixture of gases, with a molar relation of propane: oxygen: helium: water=4:8:58:30, at a reaction temperature of 380° C. and a contact time of 9.6 s. The results obtained are shown in table 2. From the results obtained it was shown that the properties of these catalyst systems depend on the quantity of copper incorporated in the catalyst.

EXAMPLE 7

Preparation of an Oxidation Catalyst Similar to That in Example 1 to Which a Greater Amount of Copper Was Added 120.0 g of tetra-hydrated ammonium hepta-molybdate, 23.80 g of ammonium methavanadate and 35.96 g of telluric acid were dissolved in 1960 ml of hot water at 80° C. obtaining a uniform solution. On the other hand, and after heating to 40° C., a solution (535.2 g) of niobium oxalate was prepared which contained 80.96 millimoles of niobium and added to the previous solution obtaining a solution. The water was removed from this solution by evaporation with a Rotavapor at 50° C. obtaining a solid. This solid was dried in a stove at 110° C. for 24 hours and ground until it reached particle sizes of less than 0.25 mm. The resulting powder was calcined at 600° C. for 2 hours in a nitrogen environment.

10.0 g of the solid, obtained in the same way as in example 1, were mixed with 10.0 ml of an aqueous solution with 0.458 g of copper nitrate (II). The solid resulting after the evaporation of the excess water. With stirring at 80° C., was dried in a stove at 110° C. for 24 hours and ground until it reached particle sizes of less than 0.25 mm. The resulting powder was calcined at 600° C. for 1 hour in a nitrogen environment to obtain the catalyst.

EXAMPLE 8

The Use of the Catalyst Described in Example 7 for the Selective Oxidation of Propane to Acrylic Acid 6.0 g of the calcined solid described in example 5 were put in a fixed bed quartz reactor. The oxidation reaction was carried out employing a mixture of gases, with a molar relation of propane: oxygen: helium: water=4:8:58:30, at a reaction temperature of 380° C. and a contact time of 4 s. The results obtained are shown in table 2.

EXAMPLE 9

Preparation of an Oxidation Catalyst Based on a Mixed Oxide of Mo—Te—V—Cu—O 26.5 g of tetra-hydrated ammonium hepta-molybdate and 5.75 g of telluric acid were dissolved in 195.0 ml of water at 80° C. Ammonium hydroxide was then added (25% aqueous solution) up to pH=7.5. The mixture was stirred and the water left to evaporate. The solid obtained was dried at 80° C.

21.8 g of this solid were suspended in 155.0 g of water at 80° C. and 7.25 g of vanadyl sulphate and 9.05 g of oxalic acid added. The mixture was stirred and transferred to a steel autoclave with an internal lining of Teflon. The autoclave was maintained at 175° C. statically, for 2 days. The contents of the autoclave were filtered, washed with distilled water and dried at 80° C. The solid obtained was calcined at 600° C. for 2 hours in a nitrogen current to obtain the catalyst.

Figure 3:
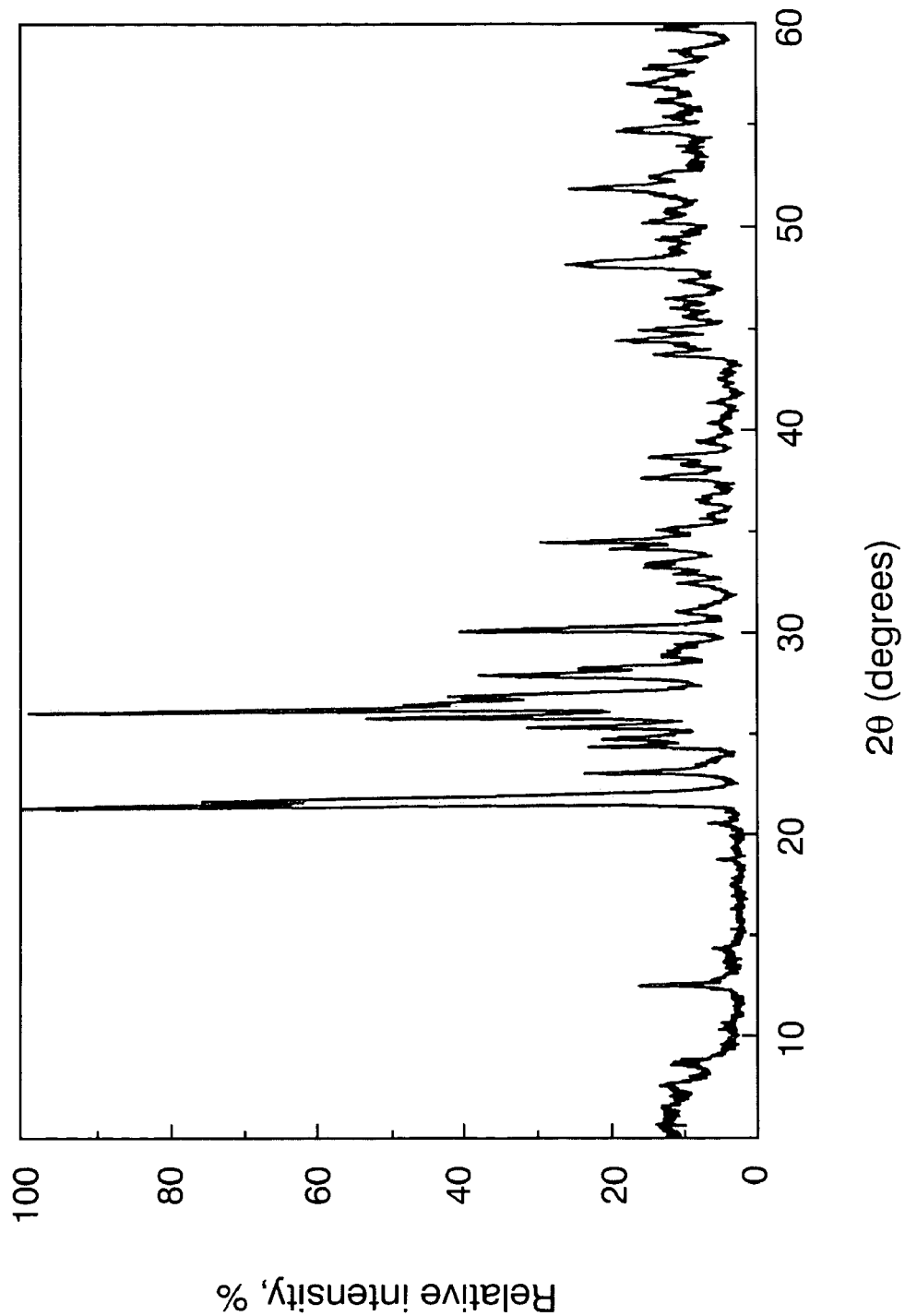

10.0 g of the calcined solid were incorporated in 10.0 ml of an aqueous solution with 0.174 g of copper nitrate (II). Once the water had evaporated, the solid resulting was dried in a stove at 110° C. for 24 hours and ground until it reached particle sizes of less than 0.25 mm. The resulting powder was calcined at 600° C. for 1 hour in a nitrogen environment to obtain the catalyst. The X-ray diffractogram of this catalyst is shown in FIG. 3.

EXAMPLE 10

Preparation of an Oxidation Catalyst Based on a Mixed Oxide of Mo—Te—V—O That Does Not Contain Copper 26.5 g of tetra-hydrated ammonium hepta-molybdate and 5.75 g of telluric acid were dissolved in 195.0 ml of water at 80° C. Ammonium hydroxide was then added (25% aqueous solution) up to pH=7.5. The mixture was stirred and the water left to evaporate. The solid obtained was dried at 80° C.

Figure 4:
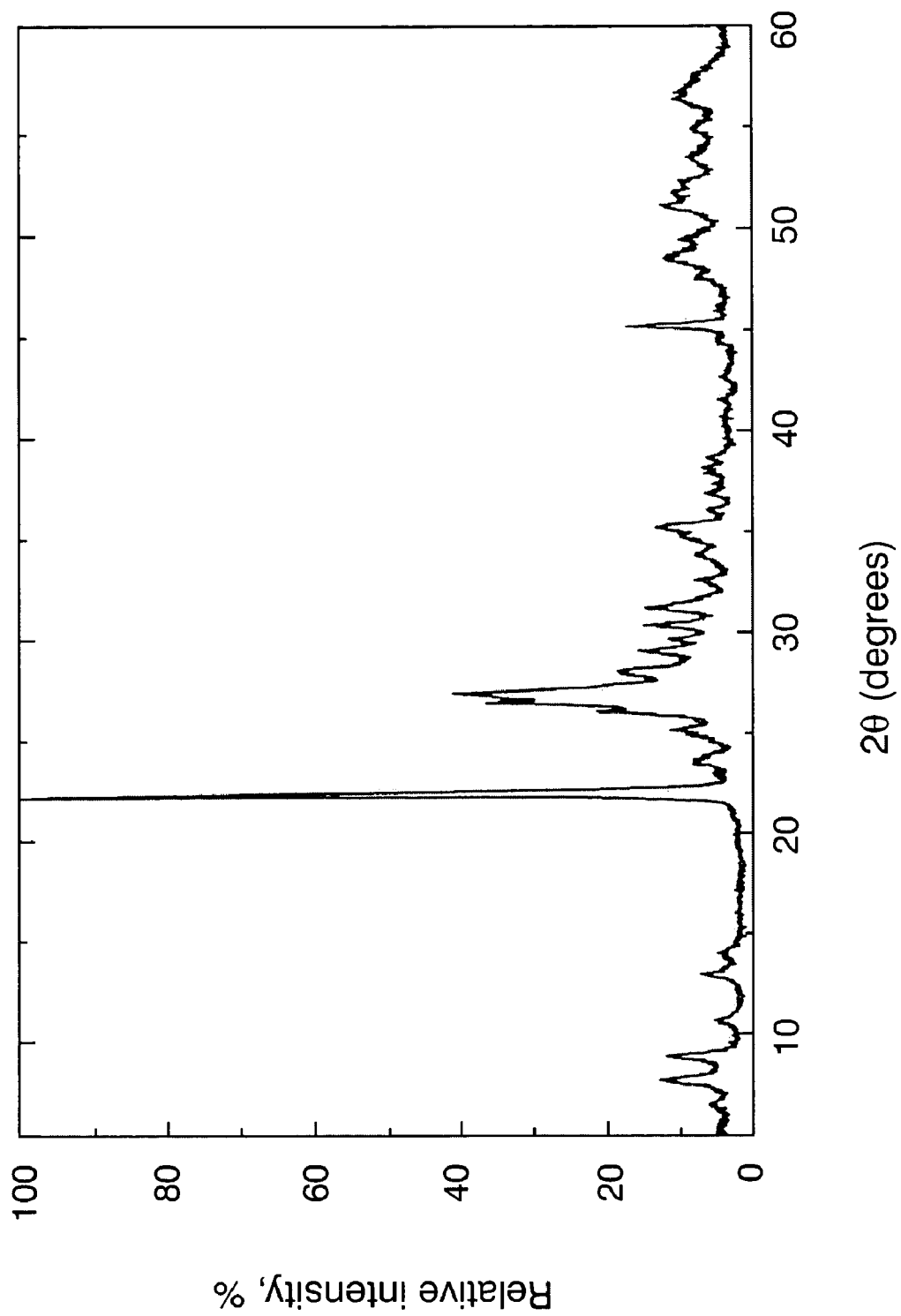

21.8 g of this solid were suspended in 155.0 g of water at 80° C. and 7.25 g of vanadyl sulphate and 9.05 g of oxalic acid added. The mixture was stirred and transferred to a steel autoclave with an internal lining of teflon. The autoclave was maintained at 175° C. statically, for 2 days. The contents of the autoclave were filtered, washed with distilled water and dried at 80° C. The solid obtained was calcined at 600° C. for 2 hours in a nitrogen current to obtain the catalyst. The X-ray diffractogram of this catalyst is shown in FIG. 4.

EXAMPLE 11

Use of the Oxidation Catalyst Described in Example 9 for the Selective Oxidation of Propane to Acrylic Acid 4.0 g of the catalyst described in example 9 were put in a fixed bed quartz reactor. The oxidation reaction was carried out employing a mixture of gases, with a molar relation of propane: oxygen: helium: water=4:8:58:30, at a reaction temperature of 380° C. and a contact time of 1.6 s. The results obtained are shown in table 3.

EXAMPLE 12

Use of the Oxidation Catalyst Described in Example 10 for the Selective Oxidation of Propane to Acrylic Acid 4.0 g of the catalyst described in example 10 were put in a fixed bed quartz reactor. The oxidation reaction was carried out employing a mixture of gases, with a molar relation of propane: oxygen: helium: water=4:8:58:30, at a reaction temperature of 380° C. and a contact time of 1.6 s. The results obtained are shown in table 3

EXAMPLE 13

Preparation of an Oxidation Catalyst Based on a Mixed Oxide of Mo—Te—V—Nb—Cu—O 26.5 g of tetra-hydrated ammonium hepta-molybdate and 5.75 g of telluric acid were dissolved in 195.0 ml of water at 80° C. Ammonium hydroxide was then added (25% aqueous solution) up to pH=7.5. The water was evaporated and the resulting solid dried at 80° C., the MT solid being obtained.

30.0 g of the MT solid was suspended in 213.30 g of water at 80° C. and 9.01 g of vanadyl sulphate and 10.39 g of niobium (V) oxalate added. The mixture was stirred and transferred to a steel autoclave with an internal lining of teflon. The autoclave was maintained at 175° C. statically, for 2 days. The contents of the autoclave were filtered, washed with distilled water and dried at 80° C. The solid obtained was calcined at 600° C. for 2 hours in a nitrogen current.

Figure 5:
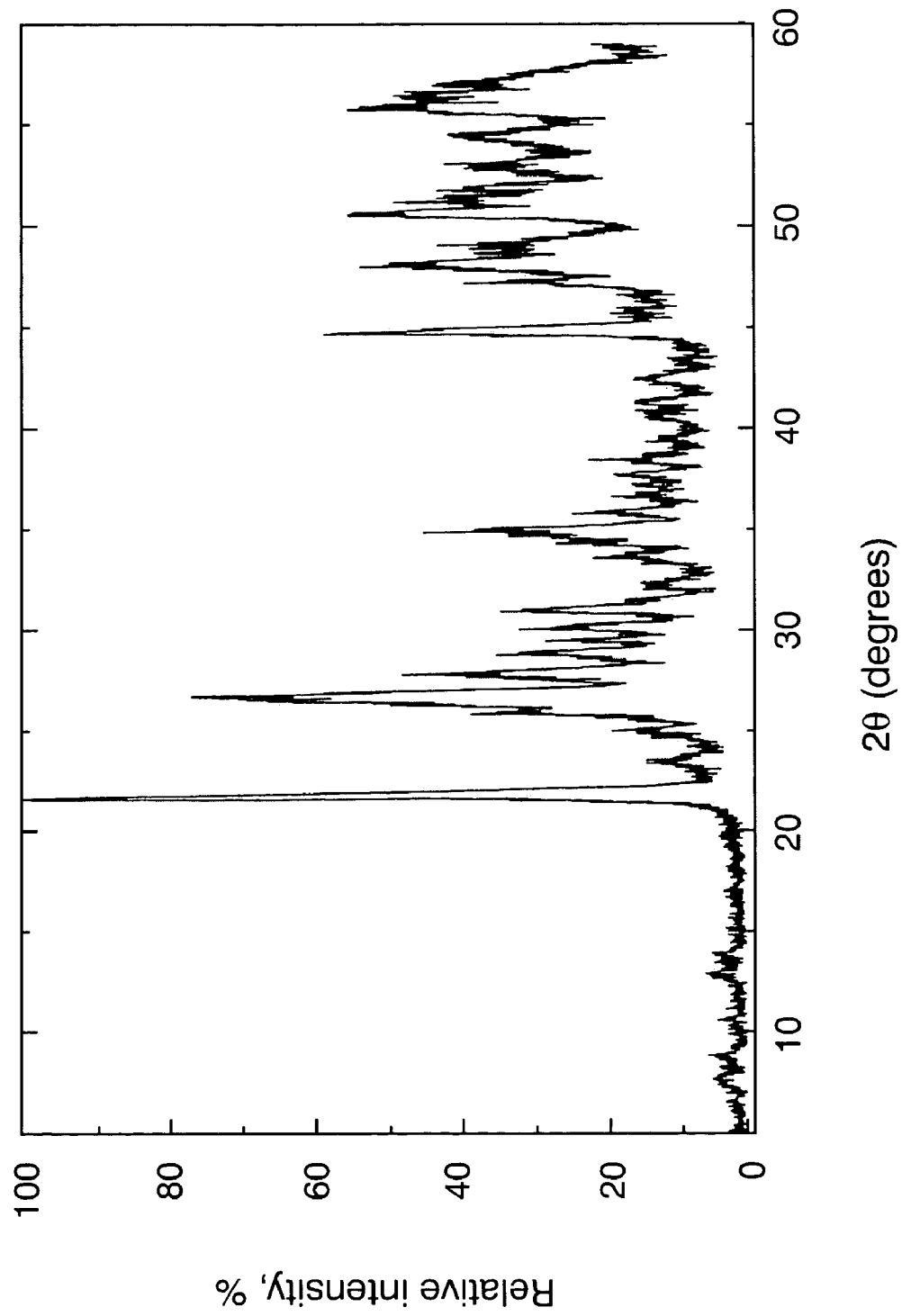

10.0 g of the calcined solid were suspended in 10.0 ml of an aqueous solution with 0.080 g of copper nitrate (II). Once the water had evaporated, the resulting solid was dried in a stove at 110° C. for 24 hours and ground until it reached particle sizes of less than 0.25 mm. The resulting powder was calcined at 600° C. for 1 hour in a nitrogen environment to obtain the catalyst The X-ray diffractogram of this catalyst is shown in FIG. 5.

EXAMPLE 14

Preparation of an Oxidation Catalyst Based on a Mixed Oxide of Mo—Te—V—Nb—O to Which Copper Was Not Incorporated 26.5 g of tetra-hydrated ammonium hepta-molybdate and 5.75 g of telluric acid were dissolved in 195.0 ml of water at 80° C. Ammonium hydroxide was then added (25% aqueous solution) up to pH=7.5. In the solution obtained, water was evaporated, with stirring at 80° C. The resulting solid was dried in a stove at 90° C., obtaining the MT solid.

Figure 6:
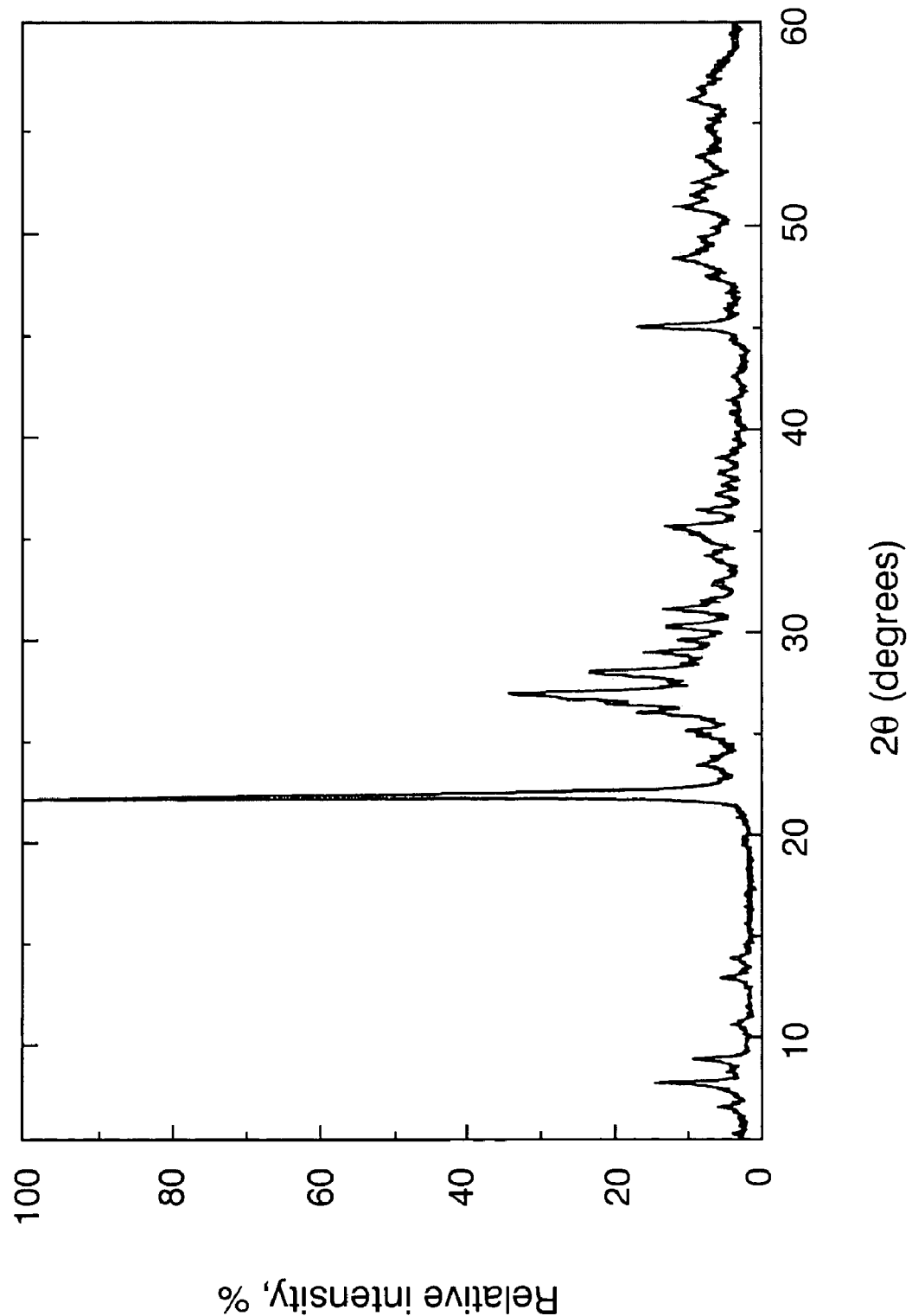

30.0 g of the MT solid were suspended in 213.30 g of water at 80° C. and 9.01 g of vanadyl sulphate and 10.39 g of niobium (V) oxalate were added. The mixture was stirred and transferred to a steel autoclave with an internal teflon cover. The autoclave was kept at 175° C., statically, for 2 days. The contents of the autoclave were filtered, washed with distilled water and dried at 80° C. The solid obtained was calcined at 600° C. for 2 hours in a nitrogen current to obtain the catalyst. This catalyst is characterised by showing an X-ray diffractogram like that shown in FIG. 6.

EXAMPLE 15

Use of the Catalyst Described in Example 13 for Selective Oxidation of Propane to Acrylic Acid 2.5 g of the calcined solid prepared in example 13 were put in a fixed bed quartz reactor. The reaction took place employing a mixture of gases, with a molar relation of propane: oxygen: helium: water=4:8:58:30, at a reaction temperature of 380° C. and a contact time of 1.6 s. The results obtained are shown in table 3.

EXAMPLE 16

Use of the Catalyst Described in Comparative Example 13 for Selective Oxidation of Propane to Acrylic Acid 2.5 g of the calcined solid prepared in example 14 were put in a fixed bed quartz reactor. The reaction took place employing a mixture of gases, with a molar relation of propane: oxygen: helium: water=4:8:58:30, at a reaction temperature of 380° C. and a contact time of 1.6 s. The results obtained are shown in table 3. From the results obtained it is shown that the inclusion of the copper in the catalyst increases both the conversion of propane and the selectivity to acrylic acid.

EXAMPLE 17

Use of the Catalyst Described in Example 13 for Selective Oxidation of Propane to Acrylic Acid With Different Reaction Conditions 2.5 g of the catalyst described in example 10 were put in a fixed bed quartz reactor. The reaction took place employing a mixture of gases, with a molar relation of propane: oxygen: helium: water=3.75:11.25:47.5:30, at a reaction temperature of 400° C. and a contact time of 3.75 s. The results obtained are shown in table 3.

EXAMPLE 18

Preparation of an Oxidation Catalyst Similar to That in Example 13 to Which a Minor Amount of Copper Was Added 26.5 g of tetra-hydrated ammonium hepta-molybdate and 5.75 g of telluric acid were dissolved in 195.0 g of water at 80° C. Then, ammonium hydroxide (25% aqueous solution) was added up to pH=7.5. The water was evaporated and the resulting solid dried in a stove at 90° C., obtaining the MT solid.

30.0 g of the MT solid were suspended in 213.30 g of water at 80° C. and 9.01 g of vanadyl sulphate and 10.39 g of niobium (V) oxalate were added. The mixture was stirred and transferred to a steel autoclave with an internal teflon cover. The autoclave was kept at 175° C., statically, for 2 days. The contents of the autoclave were filtered, washed with distilled water and dried at 80° C. The solid obtained was calcined at 600° C. for 2 hours in a nitrogen current.

10.0 g of the calcined solid were added to 10.0 ml of aqueous solution with 0.040 g of copper nitrate (II). Once the water had evaporated, the resulting solid was dried in a stove at 110° C. for 24 hours and ground until it reached particle sizes of less than 0.25 mm. The resulting powder was calcined at 600° C. for 1 hour in a nitrogen environment to obtain the catalyst.

EXAMPLE 19

Use of the Catalyst Described in Example 18 for Selective Oxidation of Propane to Acrylic Acid 2.5 g of the catalyst described in example 10 were put in a fixed bed quartz reactor. The reaction took place employing a mixture of gases, with a molar relation of propane: oxygen: helium: water=4:8:58:30, at a reaction temperature of 380° C. and a contact time of 1.6 s. The results obtained are shown in table 3.

EXAMPLE 20

Use of the Catalyst Described in Example 18 for Selective Oxidation of Propane to Acrylic Acid With Different Reaction Conditions 2.5 g of the catalyst described in example 18 were put in a fixed bed quartz reactor. The reaction took place employing a mixture of gases, with a molar relation of propane: oxygen: helium: water=3:9:38:50, at a reaction temperature of 390° C. and a contact time of 4 s. The results obtained are shown in table 3.

EXAMPLE 21

Preparation of an Oxidation Catalyst Similar to That in Example 13 to Which a Major Amount of Copper Was Added 26.5 g of tetra-hydrated ammonium hepta-molybdate and 5.75 g of telluric acid were dissolved in 195.0 g of water at 80° C. Then, ammonium hydroxide (25% aqueous solution) was added up to pH=7.5. The water was evaporated and the resulting solid dried in a stove at 90° C., obtaining the MT solid.

30.0 g of the MT solid was suspended in 213.30 g of water at 80° C. and 9.01 g of vanadyl sulphate and 10.39 g of niobium (V) oxalate were added. The mixture was stirred and transferred to a steel autoclave with an internal teflon cover. The autoclave was kept at 175° C., statically, for 2 days. The contents of the autoclave were filtered, washed with distilled water and dried at 80° C. The solid obtained was calcined at 600° C. for 2 hours in a nitrogen current.

10.0 g of the calcined solid were added to 10.0 ml of aqueous solution with 0.161 g of copper nitrate (II). Once the water had evaporated, the resulting solid was dried in a stove at 110° C. for 24 hours and ground until it reached particle sizes of less than 0.25 mm. The resulting powder was calcined at 600° C. for 1 hour in a nitrogen environment to obtain the catalyst.

EXAMPLE 22

Use of the Catalyst Described in Example 15 for Selective Oxidation of Propane to Acrylic Acid 2.5 g of the catalyst described in example 10 were put in a fixed bed quartz reactor. The reaction took place employing a mixture of gases, with a molar relation of propane: oxygen: helium: water=4:8:58:30, at a reaction temperature of 380° C. and a contact time of 1.6 s. The results are shown in table 3. The results obtained show that the catalytic properties of these catalysts depend on the copper contents in the catalyst.

EXAMPLE 23

Use of the Catalyst Described in Example 15 for Selective Oxidation of Propane to Acrylic Acid With Different Reaction Conditions 2.5 g of the catalyst described in example 15 were put in a fixed bed quartz reactor. The reaction took place employing a mixture of gases, with a molar relation of propane: oxygen: helium: water=3:9:38:50, at a reaction temperature of 390° C. and a contact time of 4.0 s. The results are shown in table 3.

EXAMPLE 24

Preparation of an Oxidation Catalyst Similar to That in Example 13 With a Lower Mo:V Ratio 31.80 g of tetra-hydrated ammonium hepta-molybdate and 6.90 g of telluric acid were dissolved in 234.0 g of water at 80° C. Then, ammonium hydroxide (25% aqueous solution) was added up to pH=7.5. The water was evaporated in a Rotavapor at 80° C., obtaining a white solid.

30.0 g of this solid were suspended in 213.30 g of water at 80° C. and 29.9 g of vanadyl sulphate and 15.6 g of niobium (V) oxalate were added. The mixture was stirred and transferred to a steel autoclave with an internal Teflon cover. The autoclave was kept at 175° C., statically, for 2 days. The contents of the autoclave were filtered, washed with distilled water and dried at 80° C. The solid obtained was calcined at 600° C. for 2 hours in a nitrogen current.

14.0 g of the calcined solid in example 11 were added to 14.0 ml of aqueous solution with 0.190 g of copper nitrate (II). Once the water had evaporated, the resulting solid was dried in a stove at 110° C. for 24 hours and ground until it reached particle sizes of less than 0.25 mm. The resulting powder was calcined at 600° C. for 1 hour in a nitrogen environment to obtain the catalyst.

EXAMPLE 25

Preparation of an Oxidation Catalyst Similar to That in Example 24 But Without Incorporating Copper 31.80 g of tetra-hydrated ammonium hepta-molybdate and 6.90 g of telluric acid were dissolved in 234.0 g of water at 80° C. Then, ammonium hydroxide (25% aqueous solution) was added up to pH=7.5. The water was evaporated in a Rotavapor at 80° C., obtaining a white solid.

30.0 g of this solid were suspended in 213.30 g of water at 80° C. and 29.9 g of vanadyl sulphate and 15.6 g of niobium (V) oxalate were added. The mixture was stirred and transferred to a steel autoclave with an internal Teflon cover. The autoclave was kept at 175° C., statically, for 2 days. The contents of the autoclave were filtered, washed with distilled water and dried at 80° C. The solid obtained was calcined at 600° C. for 2 hours in a nitrogen current to obtain the catalyst.

EXAMPLE 26

Use of the Catalyst Described in Example 24 for Selective Oxidation of Propane to Acrylic Acid 2.0 g of the calcined solid were put in a fixed bed quartz reactor. The reaction took place employing a mixture of gases, with a molar relation of propane: oxygen: helium: water=4:8:58:30, at a reaction temperature of 380° C. and a contact time of 1.6 s. The results are shown in table 4.

EXAMPLE 27

Use of the Catalyst Described in Comparative Example 25 for Selective Oxidation of Propane to Acrylic Acid 2.0 g of the calcined solid were put in a fixed bed quartz reactor. The reaction took place employing a mixture of gases, with a molar relation of propane: oxygen: helium: water=4:8:58:30, at a reaction temperature of 380° C. and a contact time of 1.6 s. The results obtained are shown in table 4.

EXAMPLE 28

Preparation, Under Hydrothermal Conditions, of an Oxidation Catalyst Based on a Mixed Mo—Te—V—Nb—Cu—O Oxide 20.00 g of tetra-hydrated ammonium hepta-molybdate, 4.34 g of telluric acid and 9.12 g of copper nitrate (II) were dissolved in 180 ml of water at 80° C. The mixture was stirred and, later, the water was left to evaporate. The solid obtained was dried at 100° C.

Figure 7:
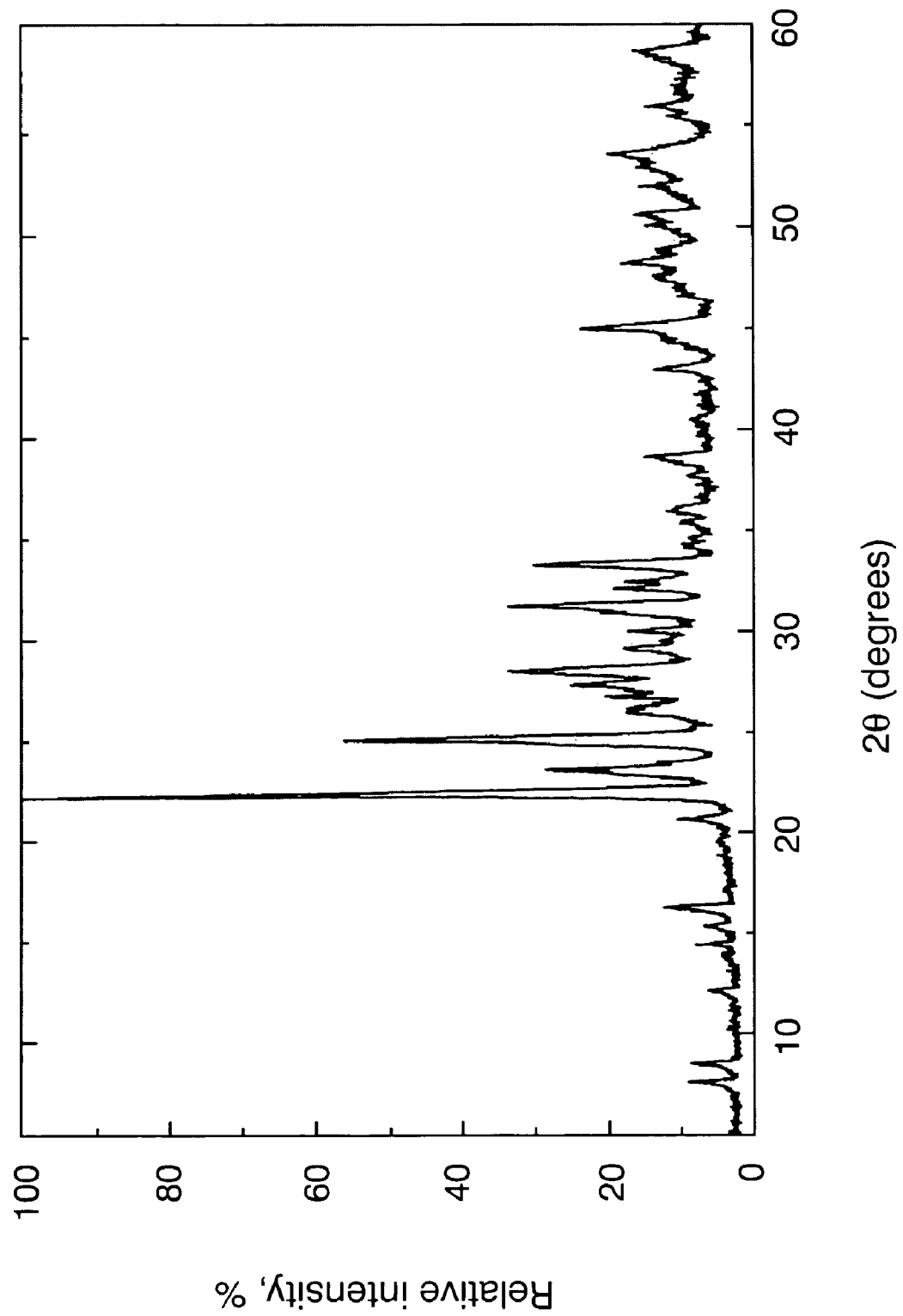

16.24 g of this solid were suspended in 106.65 g of water at 80° C. and 4.51 g of vanadyl sulphate and 5.19 g of niobium (V) oxalate were added. The mixture was stirred and transferred to a steel autoclave with an internal Teflon cover. The autoclave was kept at 175° C., statically, for 2 days. The contents of the autoclave were filtered, washed with distilled water and dried at 80° C. The solid obtained was calcined at 600° C. for 2 hours in a nitrogen current to obtain the catalyst. FIG. 7 shows the X-ray diffractogram of the catalyst.

EXAMPLE 29

Use of the Catalyst Described in Comparative Example 28 for Selective Oxidation of Propane to Acrylic Acid 2.0 g of this solid were put in a fixed bed quartz reactor. The reaction took place employing a mixture of gases, with a molar relation of propane: oxygen: helium: water=4:8:58: 30, at a reaction temperature of 380° C. and a contact time of 1.6 s. The results obtained are shown in table 4.

EXAMPLE 30

Preparation, Under Hydrothermal Conditions, of an Oxidation Catalyst Similar to That in Example 28 With a Greater Mo:Cu Ratio 10.00 g of tetra-hydrated ammonium hepta-molybdate, 2.17 g of telluric acid and 4.56 g of copper nitrate (II) were dissolved in 90 ml of water at 80° C. The mixture was left to evaporate while stirring at 80° C. The solid obtained was dried at 100° C. for 16 hours. A turquoise green coloured solid was obtained that was denominated solid A.

10.60 g of tetra-hydrated ammonium hepta-molybdate and 2.30 g of telluric acid were dissolved in 78.00 g of water at 80° C. Then, ammonium hydroxide (25% aqueous solution) was added up to pH=7.5, stirred for 1 hour and left to evaporate, while stirring at 80° C. The solid obtained was dried at 80° C. for 16 hours, obtaining a white solid that was denominated solid B.

Figure 8:
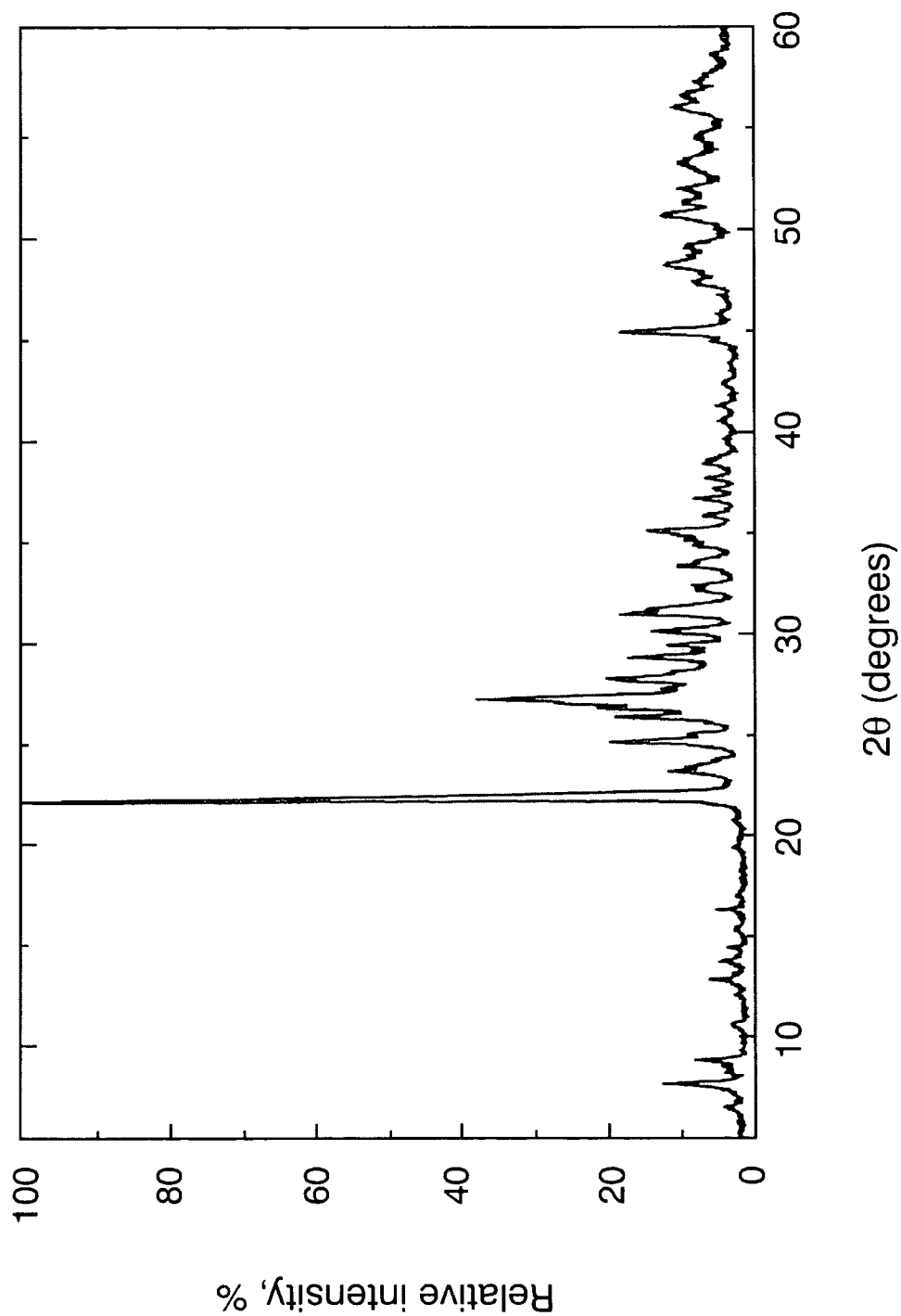

2.72 g of solid A and 12.56 g of solid B were suspended in 106.65 g of water at 80° C. and 4.91 g of vanadyl sulphate and 5.19 g of niobium (V) oxalate were added. The mixture was stirred and transferred to a steel autoclave with an internal Teflon cover. The autoclave was kept at 175° C., statically, for 2 days. The contents of the autoclave were filtered, washed with distilled water and dried at 80° C. The solid obtained was calcined at 600° C. for 2 hours in a nitrogen current to obtain the catalyst. The calcined compound shows an $Mo_{1.0}Te_{0.17}V_{0.3}Nb_{0.12}Cu_{0.05}O_n$ stoichiometry with an X-ray diffractogram like that shown in FIG. 8.

EXAMPLE 31

Use of the Catalyst Described in Comparative Example 30 for Selective Oxidation of Propane to Acrylic Acid 2.0 g of this solid were put in a fixed bed quartz reactor. The reaction took place employing a mixture of gases, with a molar relation of propane: oxygen: helium: water=4:8:58:30, at a reaction temperature of 380° C. and a contact time of 1.6 s. The results obtained are shown in table 4.

EXAMPLE 32

Use of the Catalyst Described in Example 13 for Selective Oxidation of Propylene to Acrylic Acid 1.5 g of the catalyst described in example 13 was put in a fixed bed quartz reactor. The reaction was carried out employing a mixture of gases, with a molar relation of propylene: oxygen: helium: water=2:8:80:10, at a reaction temperature of 380° C. and a contact time of 0.1 s. The results are shown in table 4.

EXAMPLE 33

Use of the Catalyst Described in Example 14 for Selective Oxidation of Propylene to Acrylic Acid 1.5 g of the catalyst of example 14 was put in a fixed bed quartz reactor. The reaction was carried out employing a mixture of gases, with a molar relation of propylene: oxygen: helium: water=2:8:80:10, at a reaction temperature of 380° C. and a contact time of 0.2 s. The results are shown in table 5.

EXAMPLE 34

Use of the Catalyst Used in Example 32 for Selective Oxidation of Propylene to Acrylic Acid in Which the Reaction Conditions Were Modified 2.5 g of the catalyst of example 13 were put in a fixed bed quartz reactor. The reaction was carried out employing a mixture of gases, with a molar relation of propylene: oxygen: helium: water=2:8:80:10, at a reaction temperature of 380° C. and a contact time of 0.8 s. The results are shown in table 5.

TABLE 2

Catalytic results for selective oxidation of propane to acrylic acid

| Example | Molar Ratio Mo/Te/V/Nb | Cu % | Temperature ° C. | Propane Conversion (%) | Propylene Selectivity (%) | AA Selectivity (%)[1] | AA Efficiency (%)[1] |
|---|---|---|---|---|---|---|---|
| Example 2 | 1/0, 23/0, 3/0, 12 | 1.6 | 380 | 23.7 | 8.5 | 42.0 | 10.0 |
| Example 4 | 1/0, 23/0, 3/0, 12 | 0 | 380 | 25.4 | 7.5 | 25.3 | 6.4 |
| Example 6 | 1/0, 23/0, 3/0, 12 | 0.8 | 380 | 22.0 | 10.5 | 26.9 | 5.9 |
| Example 8 | 1/0, 23/0, 3/0, 12 | 2.4 | 380 | 20.3 | 11.0 | 14.9 | 3.0 |

[1]AA = Acrylic Acid

TABLE 3

Catalytic results for selective oxidation of propane to acrylic acid

| Example | Molar Ratio Mo/Te/V/Nb | Cu % | Temperature ° C. | Propane Conversion (%) | Propylene Selectivity (%) | AA Selectivity (%)[1] | AA Efficiency (%)[1] |
|---|---|---|---|---|---|---|---|
| Example 11 | 1/0, 17/0, 30/0 | 0.9 | 380 | 33.6 | 5.8 | 20.3 | 6.8 |
| Example 12 | 1/0, 17/0, 30/0 | 0 | 380 | 32.1 | 5.5 | 13.4 | 4.3 |

TABLE 3-continued

Catalytic results for selective oxidation of propane to acrylic acid

| Example | Molar Ratio Mo/Te/V/Nb | Cu % | Temperature °C. | Propane Conversion (%) | Propylene Selectivity (%) | AA Selectivity (%)[1] | AA Efficiency (%)[1] |
| --- | --- | --- | --- | --- | --- | --- | --- |
| Example 15 | 1/0, 17/0, 30/0, 12 | 0.50 | 380 | 36.8 | 5.3 | 68.6 | 25.2 |
| Example 16 | 1/0, 17/0, 30/0, 12 | 0 | 380 | 38.5 | 5.2 | 34.0 | 13.1 |
| Example 17 | 1/0, 17/0, 30/0, 12 | 0.50 | 400 | 71.1 | 1.3 | 54.6 | 38.8 |
| Example 19 | 1/0, 17/0, 30/0, 12 | 0.25 | 380 | 31.3 | 7.9 | 64.0 | 20.0 |
| Example 20 | 1/0, 17/0, 30/0, 12 | 0.25 | 390 | 70.8 | 1.6 | 45.9 | 32.5 |
| Example 22 | 1/0, 17/0, 30/0, 12 | 1.0 | 380 | 37.9 | 5.9 | 65.1 | 24.7 |
| Example 23 | 1/0, 17/0, 30/0, 12 | 1.0 | 390 | 65.3[1] | 2.5 | 50.3 | 32.8 |

[1]AA = Acrylic Acid

TABLE 4

Catalytic results for selective oxidation of propane to acrylic acid

| Example | Molar Ratio Mo/Te/V/Nb | Cu % | Temperature °C. | Propane Conversion (%) | Propylene Selectivity (%) | AA Selectivity (%)[1] | AA Efficiency (%)[1] |
| --- | --- | --- | --- | --- | --- | --- | --- |
| Example 26 | 1/0, 17/0, 7/0, 12 | 0.7 | 380 | 44.9 | 3.4 | 50.8 | 22.8 |
| Example 27 | 1/0, 17/0, 7/0, 12 | 0 | 380 | 49.4 | 4.2 | 35.2 | 17.4 |
| Example 29 | 1/0, 17/0, 3/0, 12 | 17.2 | 380 | 0 | — | — | — |
| Example 31 | 1/0, 17/0, 3/0, 12 | 3.0 | 380 | 21.4 | 11.4 | 18.0 | 3.9 |

[1]AA = Acrylic Acid

TABLE 5

Selective oxidation of propane to acrylic acid

| Example | Molar Ratio Mo/Te/V/Nb | Cu % | Temperature °C. | Propylene Conversion (%) | AA Selectivity (%)[1] | AA Efficiency (%)[1] |
| --- | --- | --- | --- | --- | --- | --- |
| Example 32 | 1/0, 17/0, 30/0, 12 | 0.5 | 380 | 38.6 | 83.2 | 32.1 |
| Example 33 | 1/0, 17/0, 30/0, 12 | 0 | 380 | 43.2 | 71.9 | 31.1 |
| Example 34 | 1/0, 17/0, 30/0, 12 | 0.5 | 380 | 97.2 | 78.1 | 75.3 |

[1]AA = Acrylic Acid

The invention claimed is:

1. A catalyst for an oxidation reaction of a hydrocarbon selected from the group consisting of alkanes, alkenes and mixtures thereof, said catalyst comprising Mo, Te, V and at least another A component selected from the group consisting of Nb, Ta, Sn, Se, W, Ti, Fe, Co, Ni, Cr and a rare earth, also comprising Cu, and having the empiric formula $MoTe_h V_i Cu_j A_k O_x$, in such a way that at least Mo, Te, V and Cu are present in the form of at least one oxide and which, in the calcined form, shows an X-ray diffractogram with five intense diffraction lines corresponding to diffraction angles of 2θ at 22.1+−0.4, 27.1+−0.4; 28.1+−0.4, 36.0+−0.4 and 45.1+−0.4, wherein h, i, i, k are between 0.001 and 4.0 and x depends on the oxidation status or valency of the Mo, Te, V, Cu and A elements.

2. A catalyst according to claim 1, wherein h and i are comprised between 0.01 and 3, the i/h ratio is comprised between 0.3 and 1, and j and k are comprised between 0.001 and 2.

3. A catalyst according to claim 1, wherein A is Nb or Ta, and h and i are comprised between 0.02 and 2, the i/h ratio is comprised between 0.3 and 1, and j is comprised between 0.001 and 0.5 and k is comprised between 0.001 and 2.

4. A catalyst according to claim 1, wherein said catalyst shows an X-ray diffractogram corresponding to

| 2θ angle of diffraction (±0.4) | Average spacing (Å) | Relative intensity |
|---|---|---|
| 22.1 | 4.02 | 100 |
| 27.1 | 3.29 | 20-120 |
| 28.1 | 3.17 | 20-120 |
| 36.0 | 2.49 | 10-50 |
| 45.1 | 2.01 | 10-60. |

5. A catalyst according claim 1, wherein said catalyst is a mixed calcined oxide.

6. A catalyst according to claim 1, wherein said catalyst is a mixed oxide supported on a solid.

7. A catalyst according to claim 6, wherein the solid is selected from silica, aluminium oxide, titanium oxide and mixtures of these.

8. A catalyst according to claim 6, wherein the solid is silica contained in a ratio of 20 to 70% of the total weight of the catalyst.

9. A catalyst according to claim 1, wherein said catalyst is a mixed oxide supported on silicon carbide.

* * * * *